United States Patent
Sabelle et al.

(10) Patent No.: US 11,406,579 B2
(45) Date of Patent: Aug. 9, 2022

(54) USE OF DIHYDROISOQUINOLINIUM DOUBLE DERIVATIVES FOR TREATING KERATIN MATERIALS, COMPOSITIONS AND IMPLEMENTATION PROCESSES

(71) Applicant: L'OREAL, Paris (FR)

(72) Inventors: Stéphane Sabelle, Aulnay-sous-Bois (FR); Aziz Fadli, Aulnay-sous-Bois (FR)

(73) Assignee: L'OREAL, Paris (FR)

( * ) Notice: Subject to any disclaimer, the term of this patent is extended or adjusted under 35 U.S.C. 154(b) by 195 days.

(21) Appl. No.: 16/064,129

(22) PCT Filed: Dec. 23, 2016

(86) PCT No.: PCT/EP2016/082578
§ 371 (c)(1),
(2) Date: Jun. 20, 2018

(87) PCT Pub. No.: WO2017/109184
PCT Pub. Date: Jun. 29, 2017

(65) Prior Publication Data
US 2018/0369105 A1    Dec. 27, 2018

(30) Foreign Application Priority Data

Dec. 23, 2015 (FR) ..................... 1563275

(51) Int. Cl.
| | |
|---|---|
| *A61K 8/49* | (2006.01) |
| *C07D 401/06* | (2006.01) |
| *A61K 8/22* | (2006.01) |
| *A61K 8/38* | (2006.01) |
| *A61Q 5/08* | (2006.01) |
| *A61Q 5/10* | (2006.01) |

(52) U.S. Cl.
CPC .............. *A61K 8/4926* (2013.01); *A61K 8/22* (2013.01); *A61K 8/38* (2013.01); *A61Q 5/08* (2013.01); *A61Q 5/10* (2013.01); *C07D 401/06* (2013.01)

(58) Field of Classification Search
CPC .......... A61K 8/4926; A61K 8/22; A61K 8/38; A61K 2800/4322; C07D 401/06; A61Q 5/08; A61Q 5/10; A61Q 5/065
See application file for complete search history.

(56) References Cited

U.S. PATENT DOCUMENTS

| | | |
|---|---|---|
| 2006/0156488 A1 | 7/2006 | Herve et al. |
| 2011/0056508 A1 | 3/2011 | Gross et al. |
| 2011/0146005 A1 | 6/2011 | Gross et al. |

FOREIGN PATENT DOCUMENTS

| | | |
|---|---|---|
| EP | 1672033 A2 | 6/2006 |
| GB | 1125619 A | 8/1968 |
| WO | 0116273 A1 | 3/2001 |
| WO | 2008/025240 A1 | 3/2008 |
| WO | 2009/043613 A1 | 4/2009 |
| WO | 2017/109183 A1 | 6/2017 |
| WO | 2017/109185 A1 | 6/2017 |

OTHER PUBLICATIONS

Copp Experimentia, Neuromuscular Blocking Agents, p. 47 (Year: 1972).*
Non-Final Office Action for co-pending U.S. Appl. No. 16/064,291, dated Mar. 22, 2019.
Final Office Action for co-pending U.S. Appl. No. 16/064,291, dated Sep. 3, 2019.
Non-Final Office Action for copending U.S. Appl. No. 16/064,291, dated Jun. 18, 2020.
International Search Report for counterpart Application No. PCT/EP2016/082577, dated May 11, 2017.
International Search Report for counterpart Application No. PCT/EP2016/082580, dated Mar. 6, 2017.
Cannon, et al., "Polyphosphoric Acid in the Bischler-Napieralski Reaction," Journal of the American Pharmaceutical Association, Scientific Edition A8, XP009190223, vol. 47, 1958, pp. 353-355.
Copp, F.C. et al., "Two New Short-Acting Nondepolarizing Neuromusclar Blocking Agents," Experientia, Springer Basel AG, CH, vol. 28, No. 1, Jan. 1, 1972, pp. 47-48.
Hughes, R., "Evaluation of the Neuromuscular Blocking Properties and Side-Effects of the Two New Isoquinolinium Bisquaternary Compounds (BW.252C64 and BW.403C65)," British Journal of Anaesthesia, vol. 44, No. 27, Jan. 1, 1972, pp. 27-42.
Stenlake, John B. et al., "Bis-3, 4-Dihydroisoquinolinium Salts as Potential Neuromuscular Blocking Agents," Chimie Therapeutique, Editions Dimeo, Arcueil, Fr, vol. 16, No. 6, Jan. 1, 1981, pp. 503-507.
Szántay, Csaba et al., "Beiträge zur Chemie der Heterocyclishchen, Pseudobasischen Aminocarbinole, XXV. Redoxprozesse bei aus Bis-[3.4-dihydro-isochinolinium]-Salzen freisetzbaren Basen," Chemische Berichte, vol. 96, No. 7, Jul. 1, 1963, pp. 1779-1787 (translation not available).

(Continued)

*Primary Examiner* — Matthew P Coughlin
*Assistant Examiner* — Thurman Wheeler
(74) *Attorney, Agent, or Firm* — The Marbury Law Group, PLLC

(57) ABSTRACT

The present invention relates to the use of one or more dihydroisoquinolinium double salts for treating keratin materials, in particular keratin fibres, especially human keratin fibres such as the hair. The invention also relates to a process for treating keratin materials using said salts and optionally in the presence of one or more chemical oxidizing agents. A subject of the invention is also a composition for lightening keratin materials, comprising one or more dihydroisoquinolinium double salts as defined below and one or more chemical oxidizing agents. The present invention also relates to one or more particular dihydroisoquinolinium double salts and also to compositions containing them, in particular compositions comprising a physiologically acceptable medium.

7 Claims, No Drawings

(56) References Cited

OTHER PUBLICATIONS

International Search Report for Application No. PCT/EP2016/082578, dated Feb. 22, 2017.
Non-Final Office Action for copending U.S. Appl. No. 16/064,256, dated Jul. 24, 2020.
Non-Final Office Action for copending U.S. Appl. No. 16/064,291, dated Dec. 10, 2020.
Final Office Action for copending U.S. Appl. No. 16/064,256, dated Feb. 11, 2021.
Non-Final Office Action for copending U.S. Appl. No. 16/064,256, dated Dec. 24, 2021.

* cited by examiner

USE OF DIHYDROISOQUINOLINIUM DOUBLE DERIVATIVES FOR TREATING KERATIN MATERIALS, COMPOSITIONS AND IMPLEMENTATION PROCESSES

CROSS REFERENCE TO RELATED APPLICATIONS

This is a national stage application of PCT/EP2016/082578, filed internationally on Dec. 23, 2016, which claims priority to French Application No. 1563275 filed on Dec. 23, 2015, both of which are incorporated by reference herein in their entireties.

The present invention relates to the use of one or more dihydroisoquinolinium double salts for treating keratin materials, in particular keratin fibres and skin, especially human keratin fibres such as the hair. The invention also relates to a process for treating keratin materials using said salts and optionally in the presence of one or more chemical oxidizing agents.

A subject of the invention is also a composition for lightening keratin materials, comprising one or more dihydroisoquinolinium double salts as defined below and one or more chemical oxidizing agents.

The present invention also relates to one or more particular dihydroisoquinolinium double salts and also to compositions containing them, in particular compositions comprising a physiologically acceptable medium.

When a person wishes to change hair colour, in particular when she wishes to obtain a colour lighter than her original colour, it is often necessary to perform lightening or bleaching of the hair. To do this, lightening or bleaching products are used. This step is optionally combined with a hair colouring step.

It is known practice to lighten or bleach keratin materials, especially keratin fibres, and in particular human keratin fibres such as the hair, with lightening or bleaching compositions containing one or more chemical oxidizing agents.

Among the chemical oxidizing agents conventionally used, mention may be made of hydrogen peroxide, compounds that can produce hydrogen peroxide by hydrolysis, such as urea peroxide or persalts such as perborates, percarbonates and persulfates, hydrogen peroxide and persulfates being particularly preferred.

The role of the chemical oxidizing agent is to degrade the melanin of the hair, which, depending on the nature of the oxidizing agent and the pH conditions, leads to more or less pronounced lightening of the fibres.

The lightening or bleaching compositions are presented in anhydrous or aqueous form and in various delivery forms: for example in the form of powders, creams, gels, foams or pastes, containing alkaline compounds such as alkaline amines or silicates, and a peroxygenated reagent such as ammonium or alkali metal persulfates, perborates or percarbonates, which are diluted at the time of use with an aqueous hydrogen peroxide composition.

The lightening or bleaching compositions may also result from the mixing, at the time of use, of an anhydrous powder containing the peroxygenated reagent with an aqueous composition containing the alkaline compounds and another aqueous composition containing hydrogen peroxide.

Moreover, the keratin materials may also be bleached by means of a standard process involving applying to said materials an aqueous composition comprising at least one oxidizing agent.

Thus, for relatively mild lightening, the oxidizing agent is generally hydrogen peroxide. When greater lightening is desired, peroxygenated salts, for instance persulfates, are usually used in the presence of hydrogen peroxide.

To make a lightening or bleaching product for keratin materials that is more effective in terms of lightening and/or speed, it is currently necessary to combine hydrogen peroxide with an alkaline agent or persulfate salts with a basic pH to obtain adequate formation of active oxygen.

However, such a combination commonly causes degradation of the keratin materials, in particular keratin fibres, and may possibly lead to varying degrees of skin irritation.

Thus, there is a real need to use compounds which do not have the drawbacks mentioned above, i.e. which can produce, under safer conditions than for persulfates, powerful lightening of keratin materials, in particular of keratin fibres, while at the same time minimizing their degradation.

The Applicant has thus discovered, surprisingly, that the use of one or more dihydroisoquinolinium double compounds of formula (I), as defined below, makes it possible especially to improve the oxidizing power of hydrogen peroxide, which leads to greater lightening of keratin materials, in particular keratin fibres, while at the same time minimizing their degradation.

In other words, the use of the compounds of formula (I) according to the invention improves the activity of hydrogen peroxide without the need to increase its concentration or the need to use persulfate salts at high concentrations, which minimizes the problems of sensitization of keratin materials.

Thus, the use of the dihydroisoquinolinium double compound(s) according to the invention leads to greater lightening of keratin materials without, however, needing to increase the strength of the oxidizing agent.

In other words, the use of the dihydroisoquinolinium double compound(s) according to the invention makes it possible to boost the oxidizing activity of chemical oxidizing agents, especially hydrogen peroxide, leading to an improvement in the lightening of keratin materials relative to the use of the chemical oxidizing agent alone.

Furthermore, the dihydroisoquinolinium double compound(s) of formula (I) in combination with an oxidizing agent, especially with hydrogen peroxide, lead to more powerful lightening of the keratin materials than an oxidizing agent alone.

A subject of the present invention is thus especially the use for treating keratin materials, such as skin, preferably keratin fibres, especially human keratin fibres such as the hair, of one or more compounds of formula (I) and also the tautomeric forms thereof, the addition salts thereof and/or the solvates thereof:

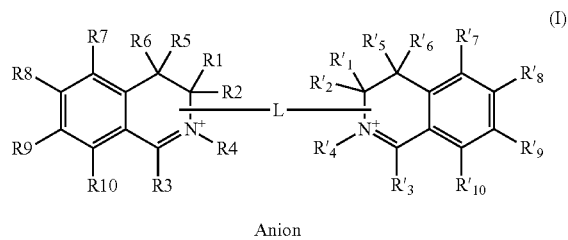

in which formula (I):
$R_1$, $R_2$, $R_3$, $R_5$, $R_6$, $R_7$, $R_8$, $R_9$, $R_{10}$, $R'_1$, $R'_2$, $R'_3$, $R'_5$, $R'_6$, $R'_7$, $R'_8$, $R'_9$ and $R'_{10}$ represent, independently of each other, a radical chosen from:
a hydrogen atom;
a halogen atom;

a $C_1$-$C_6$ alkyl radical optionally substituted with one or more groups, which may be identical or different, chosen from hydroxyl, $C_1$-$C_6$ alkoxy, cyano and amino —$NR_aR_b$ groups, a $C_1$-$C_6$ alkoxy radical;

a hydroxyl radical;

an amino radical —$NR_aR_b$, an aminocarbonyl radical —$CONH_2$, a carboxyl radical —$CO_2H$, $R_4$ and $R'_4$ represent, independently of each other:

a $C_1$-$C_6$ alkyl radical optionally substituted with one or more groups, which may be identical or different, chosen from hydroxyl, amino —$NR_aR_b$, $C_1$-$C_6$ alkoxy, cyano, aminocarbonyl —$CONH_2$ and carboxyl —$CO_2H$ groups, it being understood that a radical chosen from the radicals $R_i$ and a radical chosen from the radicals $R'_j$ together form:

a divalent radical L representing a linear or branched, saturated or unsaturated $C_1$-$C_{15}$ alkylene radical, optionally substituted with one or more hydroxyl groups and/or interrupted with one or more non-adjacent heteroatoms chosen from oxygen, nitrogen and sulfur atoms, or a covalent single bond, $R_i$ represents one of the radicals $R_1$ to $R_{10}$ and $R'_j$ represents one of the radicals $R'_1$ to $R'_{10}$; i and j denoting an integer ranging from 1 to 10, $R_a$ and $R_b$ represent, independently of each other, a hydrogen atom or a linear or branched, saturated or unsaturated $C_1$-$C_6$ alkyl radical, Anion denotes an organic or mineral anion or mixture of anions which ensures the electrical neutrality of the compounds of formula (I).

Thus, in the definition of the compounds of formula (I), a radical chosen from the radicals $R_i$ and a radical chosen from the radicals $R'_j$, i and j possibly being identical or different, together form a divalent radical L or a covalent single bond.

In other words, in the definition of the compounds of formula (I), a radical chosen from the radicals $R_1$ to $R_{10}$ and a radical chosen from the radicals $R'_1$ to $R'_{10}$ together form a divalent radical L, as defined above, or a covalent single bond.

The compound(s) of formula (I) thus defined thus correspond to dihydroisoquinolinium double salts and act as oxidation activators.

The compound(s) according to the invention may be used in the presence of one or more chemical oxidizing agents for lightening keratin materials, preferably keratin fibres, especially human keratin fibres such as the hair.

The present invention also relates to a process for treating keratin materials, preferably keratin fibres and skin, especially human keratin fibres such as the hair, which consists in applying to said materials one or more compounds of formula (I), the tautomeric forms thereof, the addition salts thereof and/or the solvates thereof.

Preferably, the process according to the invention consists in applying to keratin materials including skin and human keratin fibres, said compound(s) of formula (I), the tautomeric forms thereof, the addition salts thereof and/or the solvates thereof and one or more chemical oxidizing agents.

Moreover, a subject of the invention is a composition for lightening keratin materials, preferably keratin fibres and skin, especially human keratin fibres such as the hair, comprising one or more compounds of formula (I) and also the addition salts thereof and/or the solvates thereof, and one or more chemical oxidizing agents.

Similarly, the invention also relates to the use of said composition for lightening keratin materials, preferably keratin fibres and skin, especially human keratin fibres such as the hair.

In addition, the present invention relates to one or more compounds of formula (II), and also the tautomeric forms thereof, the addition salts thereof and/or the solvates thereof:

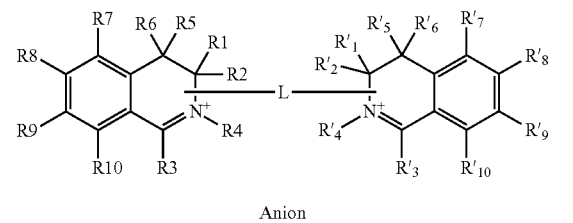

(II)

Anion in which formula (II):

$R_1$, $R_2$, $R_3$, $R_5$, $R_6$, $R_7$, $R_8$, $R_9$, $R_{10}$, $R'_1$, $R'_2$, $R'_3$, $R'_5$, $R'_6$, $R'_7$, $R'_8$, $R'_9$ and $R'_{10}$ represent, independently of each other, a radical chosen from:

a hydrogen atom;

a halogen atom;

a $C_1$-$C_6$ alkyl radical optionally substituted with one or more groups, which may be identical or different, chosen from hydroxyl, $C_1$-$C_6$ alkoxy, cyano and amino —$NR_aR_b$ groups, a $C_3$-$C_6$ alkoxy radical;

a hydroxyl radical;

an amino radical —$NR_aR_b$, an aminocarbonyl radical —$CONH_2$, a carboxyl radical —$CO_2H$, $R_4$ and $R'_4$ represent, independently of each other:

a $C_1$-$C_6$ alkyl radical optionally substituted with one or more groups, which may be identical or different, chosen from hydroxyl, amino —$NR_aR_b$, $C_1$-$C_6$ alkoxy, cyano, aminocarbonyl —$CONH_2$ and carboxyl —$CO_2H$ groups, it being understood that a radical chosen from the radicals $R_i$ and a radical chosen from the radicals $R'_j$, i being different from j, together form a divalent radical L representing:

a linear or branched, saturated or unsaturated, unsubstituted $C_4$-$C_9$ alkylene radical, a linear or branched, saturated or unsaturated $C_4$-$C_{15}$ alkylene radical substituted with one or more hydroxyl groups, a $C_1$-$C_{15}$ alkylene radical interrupted with one or more heteroatoms chosen from oxygen, nitrogen and sulfur, $R_i$ represents one of the radicals $R_1$ to $R_{10}$ and $R'_j$ represents one of the radicals $R'_1$ to $R'_{10}$; i and j denoting an integer ranging from 1 to 10, $R_a$ and $R_b$ represent, independently of each other, a hydrogen atom or a linear or branched, saturated or unsaturated $C_1$-$C_6$ alkyl radical, Anion denotes an organic or mineral anion or mixture of anions which ensures the electrical neutrality of the compounds of formula (II).

Similarly, another subject of the present invention relates to a composition comprising said compound(s) of formula (II), and also the tautomeric forms thereof, the addition salts thereof and/or the solvates thereof.

The present invention also relates to one or more compounds of formula (III), and also the tautomeric forms thereof, the addition salts thereof and/or the solvates thereof:

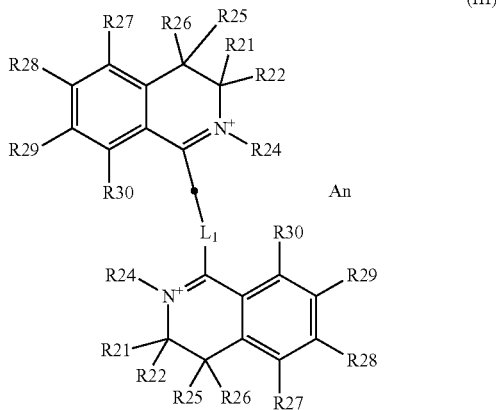

(III)

in which formula (III):
$R_{21}$, $R_{22}$, $R_{25}$ and $R_{26}$ represent, independently of each other, a radical chosen from:
a hydrogen atom;
a halogen atom,
a $C_1$-$C_6$ alkyl radical optionally substituted with one or more groups, which may be identical or different, chosen from hydroxyl, $C_1$-$C_6$ alkoxy, cyano and amino —$NR_aR_b$ groups,
a $C_1$-$C_6$ alkoxy radical;
a hydroxyl radical;
an amino radical —$NR_aR_b$,
an aminocarbonyl radical —$CONH_2$,
a carboxyl radical —$CO_2H$,
$R_{27}$, $R_{28}$, $R_{29}$ and $R_{30}$ represent, independently of each other, a radical chosen from:
a hydrogen atom;
a halogen atom,
a $C_1$-$C_6$ alkyl radical optionally substituted with one or more groups, which may be identical or different, chosen from hydroxyl, $C_1$-$C_6$ alkoxy, cyano and amino —$NR_aR_b$ groups,
a $C_3$-$C_6$ alkoxy radical;
a hydroxyl radical;
an amino radical —$NR_aR_b$,
an aminocarbonyl radical —$CONH_2$,
a carboxyl radical —$CO_2H$,
$R_{24}$ represents a $C_1$-$C_6$ alkyl radical optionally substituted with one or more groups, which may be identical or different, chosen from hydroxyl, amino —$NR_aR_b$, $C_1$-$C_6$ alkoxy, cyano, aminocarbonyl —$CONH_2$ and carboxyl —$CO_2H$ groups,
$L_1$ represents:
a linear or branched, saturated or unsaturated $C_1$-$C_{15}$ alkylene radical, optionally substituted with one or more hydroxyl groups and/or interrupted with one or more non-adjacent heteroatoms chosen from oxygen, nitrogen and sulfur atoms, or
a covalent single bond;
$R_a$ and $R_b$ represent, independently of each other, a hydrogen atom or a linear or branched, saturated or unsaturated $C_1$-$C_6$ alkyl radical,
Anion denotes an organic or mineral anion or mixture of anions which ensures the electrical neutrality of the compounds of formula (III).

The compound(s) of formula (III) thus defined thus correspond to dihydroisoquinolinium double salts which are symmetrical and which act as oxidation activators.

Similarly, another subject of the present invention relates to a composition comprising said compound(s) of formula (III), and also the tautomeric forms thereof, the addition salts thereof and/or the solvates thereof.

The present invention also relates to one or more compounds of formula (IV), and also the tautomeric forms thereof, the addition salts thereof and/or the solvates thereof:

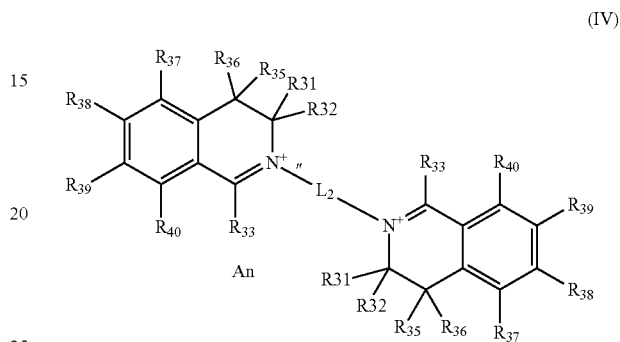

(IV)

in which formula (IV):
$R_{31}$, $R_{32}$, $R_{33}$, $R_{35}$ and $R_{36}$ represent, independently of each other, a radical chosen from:
a hydrogen atom;
a halogen atom,
a $C_1$-$C_6$ alkyl radical optionally substituted with one or more groups, which may be identical or different, chosen from hydroxyl, $C_1$-$C_6$ alkoxy, cyano and amino —$NR_aR_b$ groups,
a $C_1$-$C_6$ alkoxy radical;
a hydroxyl radical;
an amino radical —$NR_aR_b$,
an aminocarbonyl radical —$CONH_2$,
a carboxyl radical —$CO_2H$,
$R_{37}$, $R_{38}$, $R_{39}$ and $R_{40}$ represent, independently of each other, a radical chosen from:
a hydrogen atom;
a halogen atom,
a $C_1$-$C_6$ alkyl radical optionally substituted with one or more groups, which may be identical or different, chosen from hydroxyl, $C_1$-$C_6$ alkoxy, cyano and amino —$NR_aR_b$ groups,
a hydroxyl radical;
an amino radical —$NR_aR_b$,
an aminocarbonyl radical —$CONH_2$,
a carboxyl radical —$CO_2H$,
it being understood that $R_{38}$ and $R_{39}$ cannot simultaneously denote a $C_1$ alkoxy radical,
$L_2$ represents:
a linear or branched, saturated or unsaturated, unsubstituted $C_4$-$C_9$ alkylene radical,
a $C_1$-$C_{15}$ alkylene radical substituted with one or more hydroxyl groups;
a linear or branched, saturated or unsaturated $C_1$-$C_{15}$ alkylene radical interrupted with one or more non-adjacent heteroatoms chosen from oxygen, nitrogen and sulfur,
a covalent single bond,
$R_a$ and $R_b$ represent, independently of each other, a hydrogen atom or a linear or branched, saturated or unsaturated $C_1$-$C_6$ alkyl radical, Anion denotes an organic or mineral anion or mixture of anions which ensures the electrical neutrality of the compounds of formula (IV).

The compound(s) of formula (IV) thus defined thus correspond to dihydroisoquinolinium double salts which are symmetrical and which act as oxidation activators.

Similarly, another subject of the present invention relates to a composition comprising said compound(s) of formula (IV), and also the tautomeric forms thereof, the addition salts thereof and/or the solvates thereof.

Other subjects, characteristics, aspects and advantages of the invention will emerge even more clearly on reading the description and the examples that follow.

In that which follows and unless otherwise indicated, the limits of a range of values are included within this range, in particular in the expressions "of between" and "ranging from . . . to . . . ".

Moreover, the expression "at least one" used in the present description is equivalent to the expression "one or more". In addition, the expression "at least two" is equivalent to the expression "two or more".

The term "anion or mixture of anions which ensures the electrical neutrality of the compounds of formulae (I) to (IV)" means an anion or an anionic group derived from an organic or mineral acid salt which counterbalances the cationic charge of the compound; more particularly, the anionic counterion is chosen from i) a halide such as a chloride; ii) a nitrate; iii) a sulfonate including $C_1$-$C_6$ alkylsulfonates: Alk-S(O)$_2$O$^-$ such as methanesulfonate or mesylate and ethanesulfonate; iv) an arylsulfonate: Ar—S(O)$_2$O$^-$ such as benzenesulfonate and toluenesulfonate or tosylate; v) citrate; vi) succinate; vii) tartrate; viii) lactate; ix) an alkyl sulfate: Alk-O—S(O)O$^-$ such as methyl sulfate and ethyl sulfate; x) an aryl sulfate: Ar—O—S(O)O$^-$ such as benzene sulfate and toluene sulfate; xi) an alkoxy sulfate: Alk-O—S(O)$_2$O$^-$ such as methoxy sulfate and ethoxy sulfate; xii) an aryloxy sulfate: Ar—O—S(O)$_2$O$^-$, xiii) a phosphate O=P(OH)$_2$—O$^-$, O=P(O$^-$)$_2$—OH O=P(O$^-$)$_3$, HO—[P(O)(O$^-$)]$_w$—P(O)(O$^-$)$_2$ with w being an integer between 1 and 15; xiv) acetate; xv) triflate; and xvi) a borate such as tetrafluoroborate, xvii) a disulfate (O=)$_2$S(O$^-$)$_2$ or SO$_4^{2-}$; xviii) monosulfate HSO$_4^-$.

The term "non-adjacent heteroatoms" means heteroatoms that are not adjacent to each other, i.e. heteroatoms separated from each other by at least one carbon atom. Thus, the alkylene chain L, L1 or L2 in formulae (I) to (IV) is not interrupted with two continuous heteroatoms.

The term "addition salts of the compounds of formulae (I) to (IV) according to the invention" thus means addition salts with an organic or mineral acid, and addition salts with an organic or mineral base.

The "addition salts of the compounds of formulae (I) to (IV) according to the invention" are especially chosen from the addition salts with an acid, such as the hydrochlorides, hydrobromides, sulfates, citrates, succinates, tartrates, lactates, tosylates, benzenesulfonates, methanesulfonates, phosphates and acetates, and the addition salts with a base such as sodium hydroxide, potassium hydroxide, ammonia, amines or alkanolamines.

Moreover, the solvates of the compounds of formulae (I) to (IV) according to the invention more particularly represent the hydrates of said compounds and/or the combination of said compounds with a linear or branched $C_1$-$C_4$ alcohol such as methanol, ethanol, isopropanol or n-propanol. Preferably, the solvates are hydrates.

Use of the Compounds of Formula (I)

Preferably, the radicals $R_i$ and $R'_j$ are identical to each other, when i=j, with the exception of the case where $R_i$ and $R'_j$ together form a divalent radical L, as defined above, or a covalent single bond.

Preferably, $R_1$ and $R'_1$ are identical to each other, $R_2$ and $R'_2$ are identical to each other, $R_5$ and $R'_5$ are identical to each other, $R_6$ and $R'_6$ are identical to each other, $R_7$ and $R'_7$ are identical to each other, $R_8$ and $R'_8$ are identical to each other, $R_9$ and $R'_9$ are identical to each other and $R_{10}$ and $R'_{10}$ are identical to each other.

More preferentially, the radicals $R_i$ and $R'_j$ are identical to each other, when i=j, with the exception of the case where $R_i$ and $R'_j$ together form a divalent radical L, as defined above.

Preferably, a radical chosen from the radicals $R_i$ and a radical chosen from the radicals $R'_j$, when i=j, together form:
a divalent radical L representing a linear or branched, saturated or unsaturated $C_1$-$C_{15}$ alkylene radical, optionally substituted with one or more hydroxyl groups and/or interrupted with one or more non-adjacent heteroatoms chosen from oxygen, nitrogen and sulfur, or
a covalent single bond.

More preferentially, a radical chosen from the radicals $R_i$ and a radical chosen from the radicals $R'_j$, when i and j are identical and are equal to 3 or 4, together form a divalent radical L as defined above or a covalent single bond.

In other words, $R_3$ and $R'_3$ together form a divalent radical L or a covalent single bond or $R_4$ and $R'_4$ together form a divalent radical L or a covalent single bond.

Even more preferentially, a radical chosen from the radicals $R_i$ and a radical chosen from the radicals $R'_j$, when i and j are identical and are equal to 3 or 4, together form a divalent radical L as defined above.

Preferably, $R_1$, $R'_1$, $R_2$, $R'_2$, $R_3$, $R'_3$, $R_5$, $R'_5$, $R_6$, $R'_6$, $R_7$, $R'_7$, $R_8$, $R'_8$, $R_9$, $R'_9$, $R_{10}$ and $R'_{10}$ denote a hydrogen atom.

According to one variant, $R_3$ and $R'_3$ together form:
a divalent radical L representing a linear or branched, saturated or unsaturated $C_1$-$C_{15}$ alkylene radical, optionally substituted with one or more hydroxyl groups and/or interrupted with one or more non-adjacent heteroatoms chosen from oxygen, nitrogen and sulfur, or
a covalent single bond.

Preferably, $R_3$ and $R'_3$ together form a divalent radical L such that L represents a divalent radical L representing a linear or branched, saturated $C_1$-$C_{15}$ alkylene radical, one or more carbon atoms of which are optionally replaced with a heteroatom chosen from oxygen, nitrogen and sulfur, said radical L preferably denoting a divalent radical L representing a linear or branched, saturated $C_2$-$C_{10}$ alkylene radical, one or more carbon atoms of which are optionally replaced with a heteroatom chosen from oxygen, nitrogen and sulfur.

In accordance with this variant, $R_1$, $R'_1$, $R_2$, $R'_2$, $R_3$, $R'_3$, $R_5$, $R'_5$, $R_6$, $R'_6$, $R_7$, $R'_7$, $R_8$, $R'_8$, $R_9$, $R'_9$, $R_{10}$ and $R'_{10}$ preferably denote a hydrogen atom.

According to another variant, $R_4$ and $R'_4$ together form:
a divalent radical L representing a linear or branched, saturated or unsaturated $C_1$-$C_{15}$ alkylene radical, optionally interrupted with one or more non-adjacent heteroatoms chosen from oxygen, nitrogen and sulfur atoms, or
a covalent single bond.

Preferably, $R_4$ and $R'_4$ together form a divalent radical L such that L represents a linear or branched, saturated $C_1$-$C_{15}$ alkylene radical, optionally substituted with one or more hydroxyl groups and/or interrupted with one or more non-adjacent heteroatoms chosen from oxygen.

In accordance with this variant, $R_1$, $R'_1$, $R_2$, $R'_2$, $R_3$, $R'_3$, $R_5$, $R'_5$, $R_6$, $R'_6$, $R_7$, $R'_7$, $R_8$, $R'_8$, $R_9$, $R'_9$, $R_{10}$ and $R'_{10}$ preferably denote a hydrogen atom.

According to a first embodiment:
$R_1$ and $R'_1$ are identical to each other, $R_2$ and $R'_2$ are identical to each other, $R_3$ and $R'_3$ are identical to each other, $R_5$ and $R'_5$ are identical to each other, $R_6$ and $R'_6$ are identical to each other, $R_7$ and $R'_7$ are identical to each other, $R_8$ and $R'_8$ are identical to each other, $R_9$ and $R'_9$ are identical to each other, $R_{10}$ and $R'_{10}$ are identical to each other and denote, independently from one pair to another, a radical chosen from:
a hydrogen atom;
a halogen atom,
a $C_1$-$C_6$ alkyl radical optionally substituted with one or more groups, which may be identical or different, chosen from hydroxyl, cyano, $C_1$-$C_6$ alkoxy and amino $NR_aR_b$ groups,
a $C_1$-$C_6$ alkoxy radical;
a hydroxyl radical;
an amino radical $NR_aR_b$,
an aminocarbonyl radical —$CONH_2$,
a carboxyl radical —$CO_2H$,
$R_4$ and $R'_4$ together form a divalent radical L such that L represents a linear or branched, saturated or unsaturated $C_1$-$C_{15}$ alkylene radical, optionally substituted with one or more hydroxyl groups and/or interrupted with one or more non-adjacent heteroatoms chosen from oxygen, nitrogen and sulfur,
$R_a$ and $R_b$ represent, independently of each other, a hydrogen atom or a linear or branched, saturated or unsaturated $C_1$-$C_6$ alkyl radical.

In accordance with this embodiment, the preferred compounds of formula (I) are such that:
$R_1$ and $R'_1$ are identical to each other, $R_2$ and $R'_2$ are identical to each other, $R_3$ and $R'_3$ are identical to each other, $R_5$ and $R'_5$ are identical to each other, $R_6$ and $R'_6$ are identical to each other, $R_7$ and $R'_7$ are identical to each other, $R_8$ and $R'_8$ are identical to each other, $R_9$ and $R'_9$ are identical to each other, $R_{10}$ and $R'_{10}$ are identical to each other and denote, independently from one pair to another, a radical chosen from:
a hydrogen atom;
a halogen atom,
a $C_1$-$C_6$ alkyl radical optionally substituted with one or more groups, which may be identical or different, chosen from hydroxyl, cyano, $C_1$-$C_6$ alkoxy and amino $NR_aR_b$ groups,
a $C_1$-$C_6$ alkoxy radical;
a hydroxyl radical;
an amino radical $NR_aR_b$,
and, preferably, chosen from a hydrogen atom and a $C_1$-$C_4$ alkyl radical,
$R_4$ and $R'_4$ together form a divalent radical L such that L represents a saturated linear $C_2$-$C_{15}$ alkylene radical, chosen from oxygen, nitrogen and sulfur.

In accordance with this embodiment, the preferred compounds of formula (I) are such that:
$R_1$, $R'_1$, $R_2$, $R'_2$, $R_3$, $R'_3$, $R_5$, $R'5$, $R_6$, $R'_6$, $R_7$, $R'_7$, $R_8$, $R'_8$, $R_9$, $R'_9$, $R_{10}$ and $R'_{10}$ denote a hydrogen atom.
$R_4$ and $R'_4$ together form a divalent radical L such that L represents a saturated linear $C_1$-$C_{15}$ alkylene radical, optionally substituted with one or more hydroxyl groups or interrupted with one or more non-adjacent heteroatoms chosen from oxygen, nitrogen and sulfur, L preferably denoting a saturated, linear or branched $C_2$-$C_{10}$ alkylene radical, optionally substituted with one or more hydroxyl groups or interrupted with one or more non-adjacent heteroatoms chosen from oxygen.

Thus, in accordance with this first embodiment, the compound(s) according to the invention are chosen from the compounds of formula (IA), the tautomeric forms thereof, the addition salts thereof and/or the solvates thereof:

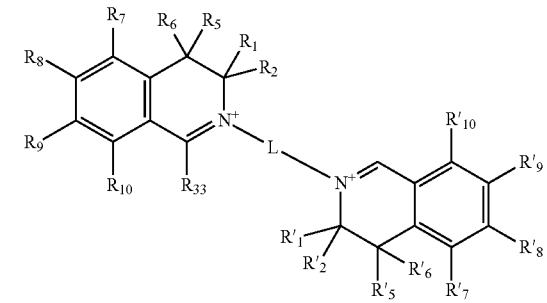

(IA)

in which formula (IA):
$R_1$, $R'_1$, $R_2$, $R'_2$, $R_3$, $R'_3$, $R_5$, $R'_5$, $R_6$, $R'_6$, $R_7$, $R'_7$, $R_8$, $R'_8$, $R_9$, $R'_9$ $R_{10}$, $R'_{10}$ and L have the same definitions as those indicated in accordance with the first embodiment.

According to this first embodiment, the compounds of formula (I), the tautomeric forms thereof, the addition salts thereof and the solvates thereof are chosen from the following compounds:

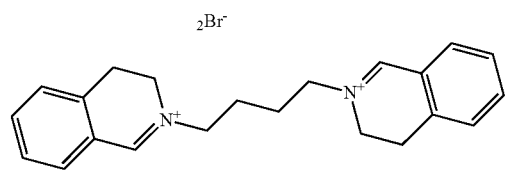 [SMILES: C1=[N+](CCCC[N+]2=Cc3ccccc3CC2)CCc2ccccc21]

2Br⁻

2,2'-butane-1,4-diyldi-3,4 dihydroisoquinolinium dibromide
Compound 1

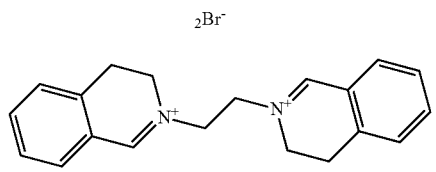 [SMILES: C1=[N+](CC[N+]2=Cc3ccccc3CC2)CCc2ccccc21]

2Br⁻

2,2'-ethane-1,4-diyldi-3,4 dihydroisoquinolinium dibromide
Compound 2

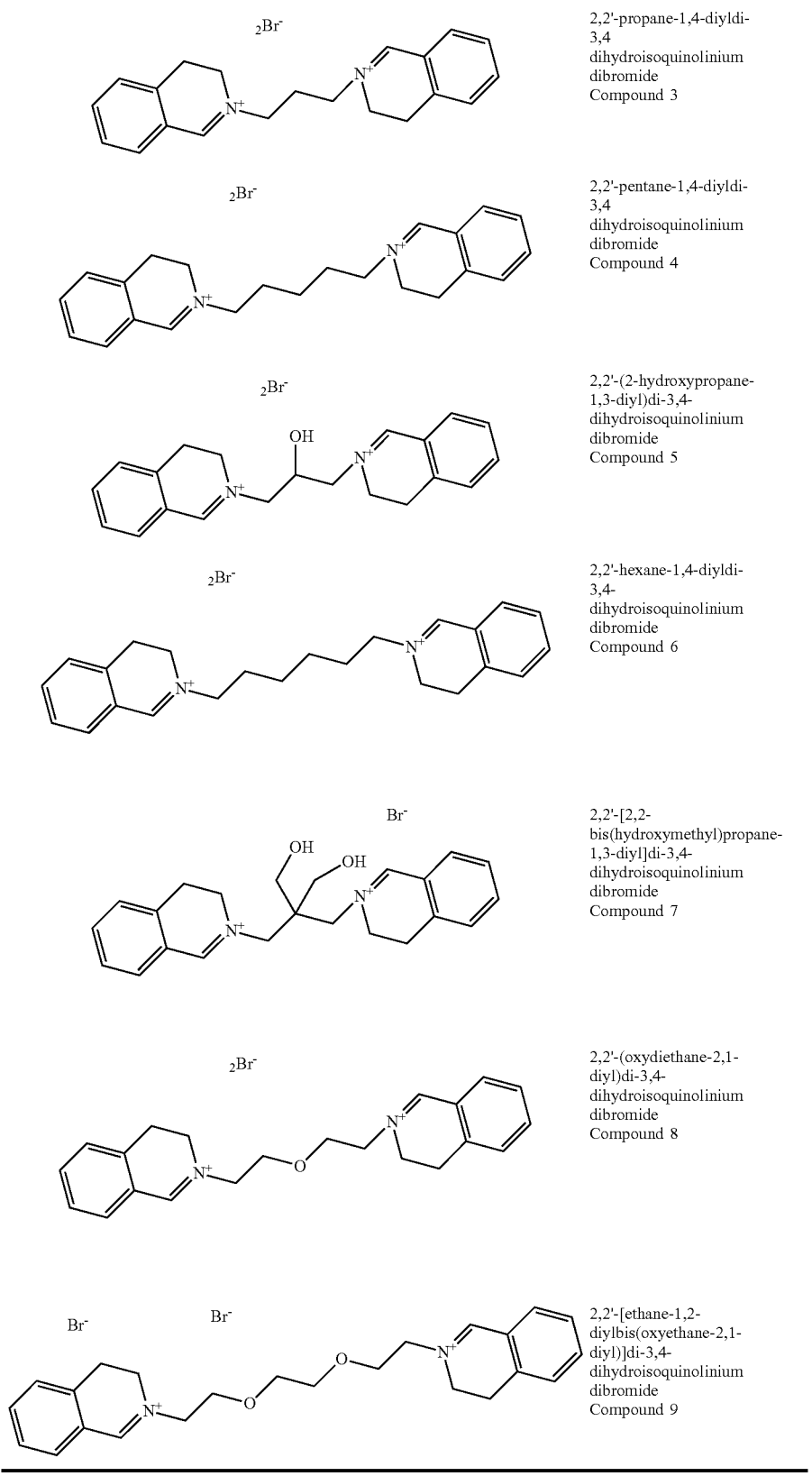

| | |
|---|---|
| | 2,2'-propane-1,4-diyldi-3,4 dihydroisoquinolinium dibromide<br>Compound 3 |
| | 2,2'-pentane-1,4-diyldi-3,4 dihydroisoquinolinium dibromide<br>Compound 4 |
| | 2,2'-(2-hydroxypropane-1,3-diyl)di-3,4-dihydroisoquinolinium dibromide<br>Compound 5 |
| | 2,2'-hexane-1,4-diyldi-3,4-dihydroisoquinolinium dibromide<br>Compound 6 |
| | 2,2'-[2,2-bis(hydroxymethyl)propane-1,3-diyl]di-3,4-dihydroisoquinolinium dibromide<br>Compound 7 |
| | 2,2'-(oxydiethane-2,1-diyl)di-3,4-dihydroisoquinolinium dibromide<br>Compound 8 |
| | 2,2'-[ethane-1,2-diylbis(oxyethane-2,1-diyl)]di-3,4-dihydroisoquinolinium dibromide<br>Compound 9 | and also mixtures thereof.

According to a second embodiment:

$R_1$ and $R'_1$ are identical to each other, $R_2$ and $R'_2$ are identical to each other, $R_5$ and $R'_5$ are identical to each other, $R_6$ and $R'_6$ are identical to each other, $R_7$ and $R'_7$ are identical to each other, $R_8$ and $R'_8$ are identical to each other, $R_9$ and $R'_9$ are identical to each other, $R_{10}$ and $R'_{10}$ are identical to each other and denote, independently from one pair to another, a radical chosen from:

a hydrogen atom;

a halogen atom, a $C_1$-$C_6$ alkyl radical optionally substituted with one or more groups, which may be identical or different, chosen from hydroxyl, cyano, $C_1$-$C_6$ alkoxy and amino $NR_aR_b$ groups, a $C_1$-$C_6$ alkoxy radical;

a hydroxyl radical;

an amino radical $NR_aR_b$, an aminocarbonyl radical —$CONH_2$, a carboxyl radical —$CO_2H$, $R_4$ and $R'_4$ are identical and represent a $C_1$-$C_6$ alkyl radical optionally substituted with one or more groups, which may be identical or different, chosen from hydroxyl, $C_1$-$C_6$ alkoxy, cyano, amino $NR_aR_b$, aminocarbonyl —$CONH_2$ and carboxyl —$CO_2H$ groups, $R_3$ and $R'_3$ together form a divalent radical L such that L represents a linear or branched, saturated or unsaturated $C_1$-$C_{15}$ alkylene radical, optionally substituted with one or more hydroxyl groups and/or interrupted with one or more non-adjacent heteroatoms chosen from oxygen, nitrogen and sulfur, $R_a$ and $R_b$ represent, independently of each other, a hydrogen atom or a linear or branched, saturated or unsaturated $C_1$-$C_6$ alkyl radical.

According to this embodiment, the preferred compounds of formula (I) are such that:

$R_1$ and $R'_1$ are identical to each other, $R_2$ and $R'_2$ are identical to each other, $R_5$ and $R'_5$ are identical to each other, $R_6$ and $R'_6$ are identical to each other, $R_7$ and $R'_7$ are identical to each other, $R_8$ and $R'_8$ are identical to each other, $R_9$ and $R'_9$ are identical to each other, $R_{10}$ and $R'_{10}$ are identical to each other and denote, independently from one pair to another, a radical chosen from:

a hydrogen atom;

a halogen atom, a $C_1$-$C_6$ alkyl radical optionally substituted with one or more groups, which may be identical or different, chosen from hydroxyl, cyano, $C_1$-$C_6$ alkoxy and amino $NR_aR_b$ groups, a $C_1$-$C_6$ alkoxy radical;

a hydroxyl radical;

an amino radical $NR_aR_b$, and, preferably, chosen from a hydrogen atom and a $C_1$-$C_4$ alkyl radical, $R_4$ and $R'_4$ are identical and represent a $C_1$-$C_6$ alkyl radical optionally substituted with one or more groups, which may be identical or different, chosen from hydroxyl, $C_1$-$C_6$ alkoxy, cyano, amino $NR_aR_b$ and aminocarbonyl —$CONH_2$ groups, preferably a $C_1$-$C_4$ alkyl radical, $R_3$ and $R'_3$ together form a divalent radical L such that L represents a linear or branched, saturated $C_1$-$C_{15}$ alkylene radical, optionally substituted with one or more hydroxyl groups and/or interrupted with one or more non-adjacent heteroatoms chosen from oxygen, nitrogen and sulfur, $R_a$ and $R_b$ represent, independently of each other, a hydrogen atom or a linear or branched, saturated or unsaturated $C_1$-$C_6$ alkyl radical.

In accordance with this embodiment, the preferred compounds of formula (I) are such that:

$R_1$, $R'_1$, $R_2$, $R'_2$, $R_5$, $R'_5$, $R_6$, $R'_6$, $R_7$, $R'_7$, $R_8$, $R'_8$, $R_9$ and $R'_9$ denote a hydrogen atom, $R_4$ and $R'_4$ are identical and represent a $C_1$-$C_6$ alkyl radical optionally substituted with one or more groups, which may be identical or different, chosen from hydroxyl, $C_1$-$C_6$ alkoxy, cyano, amino $NR_aR_b$ and aminocarbonyl —$CONH_2$ groups, preferably a $C_1$-$C_4$ alkyl radical, $R_3$ and $R'_3$ together form a divalent radical L such that L represents a linear or branched, saturated $C_1$-$C_{15}$ alkylene radical, optionally substituted with one or more hydroxyl groups or interrupted with one or more non-adjacent heteroatoms chosen from oxygen, nitrogen and sulfur, L preferably denoting a saturated, linear or branched $C_2$-$C_{10}$ alkylene radical, optionally substituted with one or more hydroxyl groups or interrupted with one or more non-adjacent heteroatoms chosen from oxygen, $R_a$ and $R_b$ represent, independently of each other, a hydrogen atom or a linear or branched, saturated or unsaturated $C_1$-$C_6$ alkyl radical.

Thus, in accordance with this second embodiment, the compound(s) according to the invention are chosen from the compounds of formula (IB), the tautomeric forms thereof, the addition salts thereof and/or the solvates thereof:

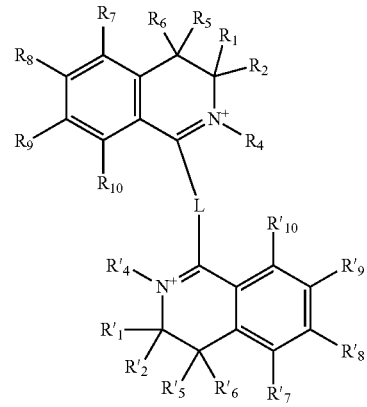

(IB)

in which formula (IB):

$R_1$, $R'_1$, $R_2$, $R'_2$, $R_5$, $R'_5$, $R_6$, $R'_6$, $R_7$, $R'_7$, $R_8$, $R'_8$, $R_9$, $R'_9$, $R_{10}$, $R'_{10}$ and L have the same definitions as those indicated in accordance with the second embodiment.

According to this second embodiment, the compounds of formula (I), the tautomeric forms thereof, the addition salts thereof and/or the solvates thereof are chosen from the following compounds:

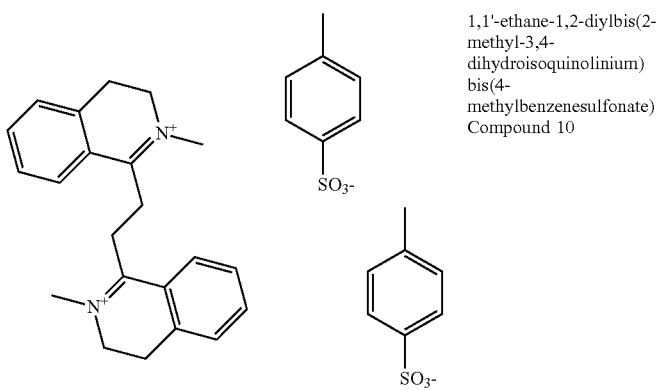
1,1'-ethane-1,2-diylbis(2-methyl-3,4-dihydroisoquinolinium) bis(4-methylbenzenesulfonate) Compound 10
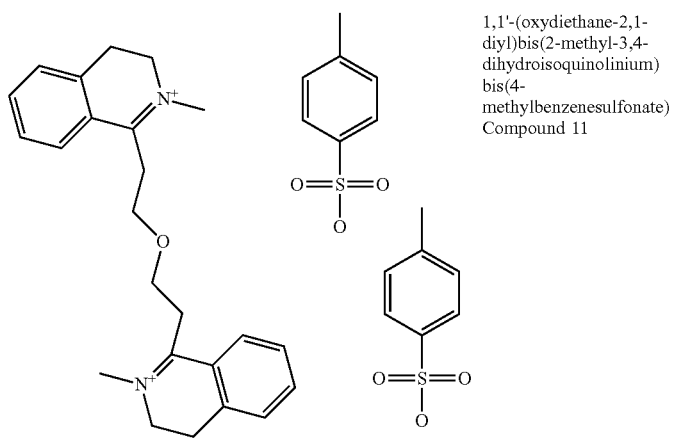
1,1'-(oxydiethane-2,1-diyl)bis(2-methyl-3,4-dihydroisoquinolinium) bis(4-methylbenzenesulfonate) Compound 11
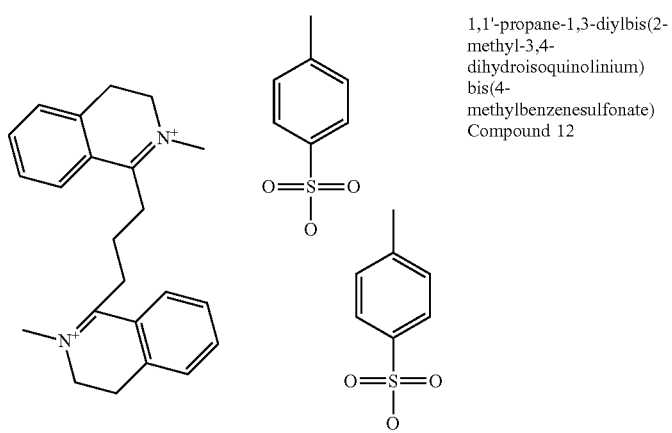
1,1'-propane-1,3-diylbis(2-methyl-3,4-dihydroisoquinolinium) bis(4-methylbenzenesulfonate) Compound 12

-continued
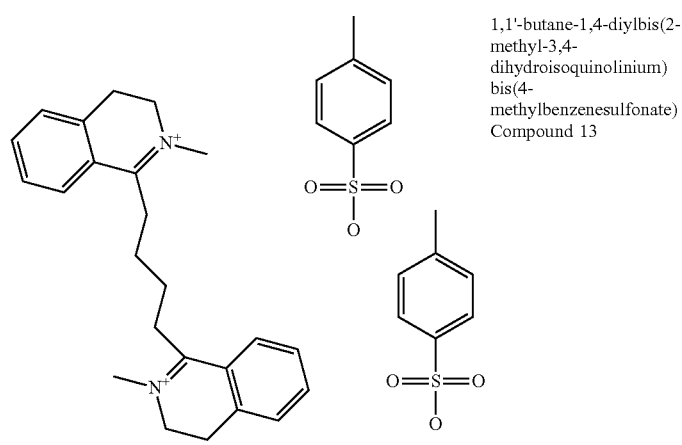
1,1'-butane-1,4-diylbis(2-methyl-3,4-dihydroisoquinolinium) bis(4-methylbenzenesulfonate)
Compound 13
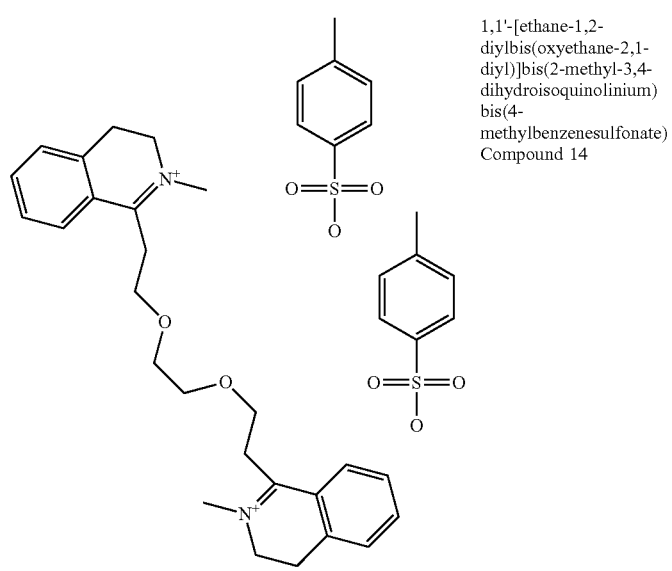
1,1'-[ethane-1,2-diylbis(oxyethane-2,1-diyl)]bis(2-methyl-3,4-dihydroisoquinolinium) bis(4-methylbenzenesulfonate)
Compound 14
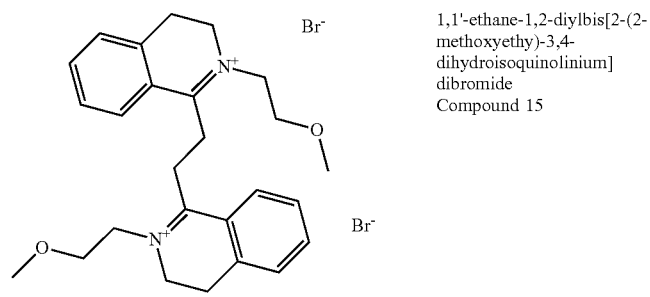
1,1'-ethane-1,2-diylbis[2-(2-methoxyethy)-3,4-dihydroisoquinolinium] dibromide
Compound 15

-continued

| | |
|---|---|
| 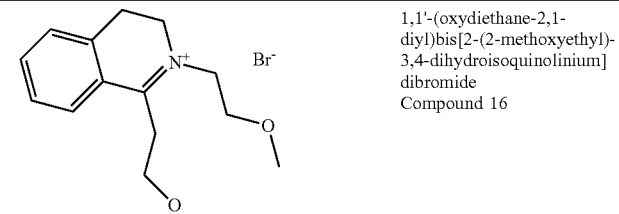 | 1,1'-(oxydiethane-2,1-diyl)bis[2-(2-methoxyethyl)-3,4-dihydroisoquinolinium] dibromide<br>Compound 16 |
| 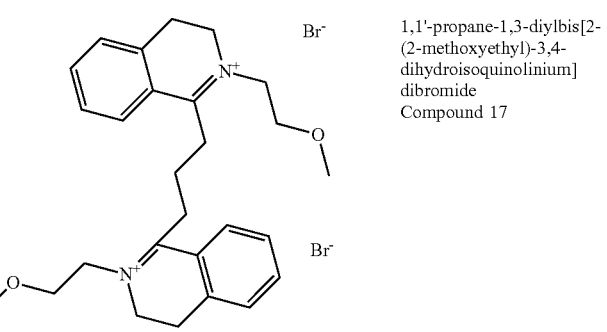 | 1,1'-propane-1,3-diylbis[2-(2-methoxyethyl)-3,4-dihydroisoquinolinium] dibromide<br>Compound 17 |
| 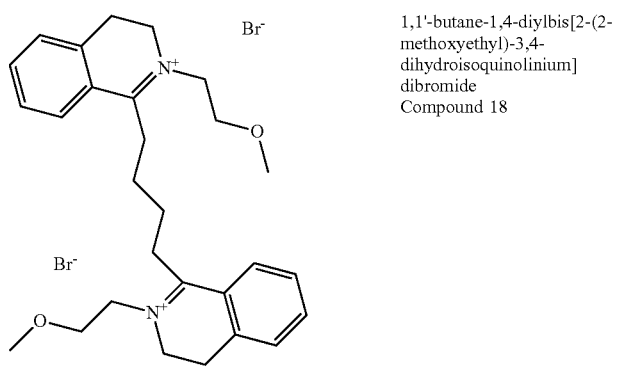 | 1,1'-butane-1,4-diylbis[2-(2-methoxyethyl)-3,4-dihydroisoquinolinium] dibromide<br>Compound 18 |
| 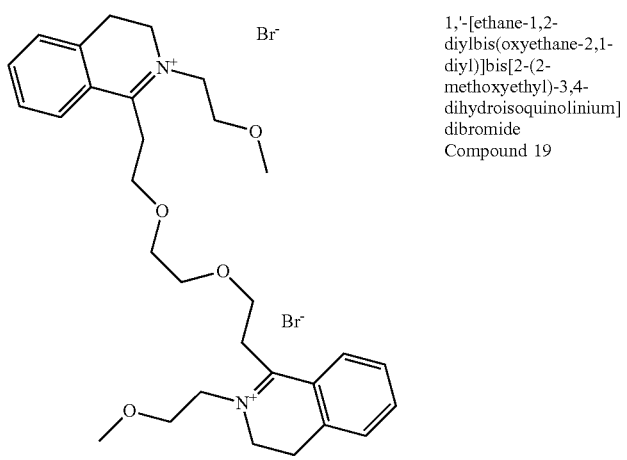 | 1,'-[ethane-1,2-diylbis(oxyethane-2,1-diyl)]bis[2-(2-methoxyethyl)-3,4-dihydroisoquinolinium] dibromide<br>Compound 19 | and also mixtures thereof.

As indicated previously, the compound(s) of formula (I) according to the invention, preferably compounds 1 to 19, may be used in the presence of one or more chemical oxidizing agents for lightening keratin materials, preferably keratin fibres, in particular human keratin fibres such as the hair.

The oxidizing agents are such as those described hereinbelow.

Composition Containing Compounds of Formula (I)

Thus, the invention relates to a composition comprising the compound(s) of formula (I) as defined above, preferably the compounds of formulae (IA) and (IB), and also the tautomeric forms thereof, the addition salts thereof and/or the solvates thereof, and one or more chemical oxidizing agents.

The composition according to the invention lightens keratin materials, especially keratin fibres and preferably human keratin fibres such as the hair, using less chemical oxidizing agent.

According to a particular embodiment of the invention, the dye composition comprises at least one chemical oxidizing agent. The expression "chemical oxidizing agent" is understood to mean an oxidizing agent other than atmospheric oxygen. The composition of the invention preferentially contains one or more chemical oxidizing agents.

The oxidizing agent(s) used in the invention are for example hydrogen peroxide, urea peroxide, alkali metal bromates, persalts such as perborates and persulfates, peracids and oxidase enzymes, among which mention may be made of peroxidases, 2-electron oxidoreductases such as uricases, and 4-electron oxygenases, for instance laccases. Hydrogen peroxide is particularly preferred.

More particularly, the chemical oxidizing agent(s) are chosen from hydrogen peroxide, urea peroxide, alkali metal bromates, peroxygenated salts, for instance persulfates, perborates, peracids and precursors thereof and percarbonates of alkali metals or alkaline-earth metals. The chemical oxidizing agent(s) advantageously consist of hydrogen peroxide.

The compound(s) of formula (I), preferably the compounds of formulae (IA) and (IB), and also the addition salts thereof and/or the solvates thereof, may be present in the composition according to the invention in a content that may range from 0.01% to 10% by weight, preferably in a content ranging from 0.5% to 3% by weight, more preferably in an content ranging from 1 to 3% by weight, relative to the total weight of the composition.

Preferentially, the chemical oxidizing agent is hydrogen peroxide.

According to one embodiment, the composition according to the invention comprises one or more compounds of formula (I), preferably the compounds of formulae (IA) and (IB), and also the tautomeric forms thereof, the addition salts thereof and/or the solvates thereof, and also at least one chemical oxidizing agent such as hydrogen peroxide.

In accordance with this embodiment, the composition preferably additionally comprises one or more persulfates.

In other words, the composition may preferentially comprise a mixture of hydrogen peroxide and persulfates.

According to one embodiment, the composition according to the invention comprises one or more compounds of formula (I), and also the tautomeric forms thereof, the addition salts thereof and/or the solvates thereof, and hydrogen peroxide, as chemical oxidizing agent; said composition being free of persulfates.

The chemical oxidizing agent(s) may be present in the composition according to the invention in a content that may range from 0.5% to 9% by weight of the ready-to-use composition, preferably in a content ranging from 1.5% to 9% by weight, relative to the total weight of the ready-to-use composition.

Preferably, the composition according to the invention may comprise one or more alkaline agents, especially organic or mineral alkaline agents.

The mineral alkaline agent(s) are preferably chosen from aqueous ammonia, ammonium halides, in particular ammonium chloride, alkali metal carbonates or bicarbonates such as sodium or potassium carbonates and sodium or potassium bicarbonates, sodium hydroxide or potassium hydroxide, or mixtures thereof.

The organic alkaline agent(s) are preferably chosen from organic amines with a $pK_b$ at 25° C. of less than 12, preferably less than 10.5. It should be noted that it is the $pK_b$ corresponding to the function of highest basicity. In addition, the organic amines do not comprise any alkyl or alkenyl fatty chain comprising more than ten carbon atoms.

The organic alkaline agent(s) are chosen, for example, from alkanolamines, oxyethylenated and/or oxypropylenated ethylenediamines, amino acids and the compounds of formula (V) below:

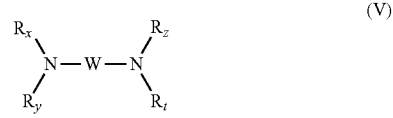

in which formula (V) W is a divalent $C_1$ to $C_6$ alkylene radical optionally substituted with one or more hydroxyl groups or a $C_1$ to $C_6$ alkyl radical, and/or optionally interrupted with one or more heteroatoms such as O, or —$NR_a$; $R_x$, $R_y$, $R_z$, $R_t$ and $R_u$, which may be identical or different, represent a hydrogen atom or a $C_1$ to $C_6$ alkyl, $C_1$ to $C_6$ hydroxyalkyl or $C_1$ to $C_6$ aminoalkyl substituent.

The term "alkanolamine" means an organic amine comprising a primary, secondary or tertiary amine function, and one or more linear or branched $C_1$ to $C_8$ alkyl groups bearing one or more hydroxyl radicals.

Organic amines chosen from alkanolamines such as monoalkanolamines, dialkanolamines or trialkanolamines comprising one to three identical or different $C_1$-$C_4$ hydroxyalkyl radicals are in particular suitable for performing the invention.

Among the compounds of this type, mention may be made of monoethanolamine (MEA), diethanolamine, triethanolamine, monoisopropanolamine, diisopropanolamine, N,N-dimethylethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethyl)aminomethane.

More particularly, the amino acids that may be used are of natural or synthetic origin, in their L, D or racemic form, and comprise at least one acid function chosen more particularly from carboxylic acid, sulfonic acid, phosphonic acid and phosphoric acid functions. The amino acids may be in neutral or ionic form.

As amino acids that can be used in the present invention, mention may be made especially of aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine and valine, and the salts thereof.

Advantageously, the amino acids are basic amino acids comprising an additional amine function optionally included in a ring or in a ureido function.

Such basic amino acids are preferably chosen from those corresponding to formula (VI) below, and also salts thereof:

$$R-CH_2-CH(NH_2)-C(O)-OH \quad (VI)$$

in which R represents a group chosen from imidazolyl, preferably imidazolyl-4-yl; aminopropyl; aminoethyl; —(CH$_2$)$_2$NH—C(O)—NH$_2$; and —(CH$_2$)$_2$—NH—C(NH)—NH$_2$.

The organic amine may also be chosen from organic amines of heterocyclic type. Besides histidine that has already been mentioned in the amino acids, mention may in particular be made of pyridine, piperidine, imidazole, triazole, tetrazole and benzimidazole.

The organic amine may also be chosen from amino acid dipeptides. As amino acid dipeptides that may be used in the present invention, mention may be made especially of carnosine, anserine and balenine.

The organic amine may also be chosen from compounds comprising a guanidine function. As amines of this type that may be used in the present invention, besides arginine, which has already been mentioned as an amino acid, mention may be made especially of creatine, creatinine, 1,1-dimethylguanidine, 1,1-diethylguanidine, glycocyamine, metformin, agmatine, N-amidinoalanine, 3-guanidinopropionic acid, 4-guanidinobutyric acid and 2-([amino(imino)methyl]amino)ethane-1-sulfonic acid.

Hybrid compounds that may be mentioned include the salts of the amines mentioned previously with acids such as carbonic acid or hydrochloric acid.

Guanidine carbonate or monoethanolamine hydrochloride may be used in particular.

Preferably, the alkaline agent(s) present in the composition according to the invention are chosen from aqueous ammonia, alkanolamines, amino acids in neutral or ionic form, in particular basic amino acids, and preferably corresponding to those of formula (VI).

More preferentially, the alkaline agent(s) present in the composition according to the invention are chosen from aqueous ammonia and alkanolamines, and mixtures thereof.

More preferentially, the alkaline agent(s) present in the composition according to the invention, are chosen from aqueous ammonia and ammonium chloride.

According to one particular embodiment of the invention, the alkaline agent(s) are mineral.

According to one particular embodiment of the invention, the alkaline agent(s) are organic such as alkanolamines particularly monoethanolamine.

The quantity of alkaline agent(s) present in the composition according to the invention may range from 0.01% to 30% by weight, and preferably from 0.1% to 20% by weight relative to the total weight of the composition.

The composition according to the invention has a pH greater than or equal to 4. Preferably, the pH of the composition according to the invention varies from 7 to 11, more preferentially from 8 to 10 and more preferentially from 8.5 to 9.5.

According to one embodiment, the composition according to the invention comprises one or more compounds of formula (II), and also the tautomeric forms thereof, the addition salts thereof and the solvates thereof, one or more chemical oxidizing agents and one or more alkaline agents chosen from aqueous ammonia and ammonium halides such as ammonium chloride.

In accordance with this embodiment, the chemical oxidizing agent is preferably hydrogen peroxide.

The composition according to the invention may optionally comprise one or more additives, different from the compounds of the invention and among which mention may be made of organic solvents, cationic, anionic, nonionic or amphoteric polymers or mixtures thereof, antidandruff agents, anti-seborrhoea agents, agents for preventing hair loss and/or for promoting hair regrowth, vitamins and provitamins including panthenol, sunscreens, mineral or organic pigments, sequestrants, plasticizers, solubilizers, acidifying agents, mineral or organic thickeners, especially polymeric thickeners, opacifiers or nacreous agents, antioxidants, hydroxy acids, fragrances, preserving agents, pigments and ceramides.

Needless to say, those skilled in the art will take care to select this or these optional additional compound(s) such that the advantageous properties intrinsically associated with the composition according to the invention are not, or are not substantially, adversely affected by the envisaged addition(s).

The above additives may generally be present in an amount, for each of them, of between 0 and 20% by weight relative to the total weight of the composition.

The composition according to the invention preferentially comprises a physiologically acceptable medium.

For the purposes of the present invention, the term "physiologically acceptable medium" is intended to denote a medium that is suitable for the topical administration of a composition. A physiologically acceptable medium is preferentially a cosmetically or dermatologically acceptable medium, i.e. a medium that has no unpleasant odour or appearance, and that is entirely compatible with the topical administration route. In the present case, where the composition is intended for topical administration, that is to say for administration by application at the surface of the keratin material under consideration, such a medium is considered in particular to be physiologically acceptable when it does not cause stinging, tightness or redness unacceptable to the user.

Treatment Process According to the Invention

The process for treating keratin materials consists in applying to said materials one or more compounds of formula (I) as defined above, the tautomeric forms thereof, the addition salts thereof and/or the solvates thereof, optionally in the presence of one or more chemical oxidizing agents.

Preferably, the compound(s) of formula (I) according to the invention are applied in the presence of one or more chemical oxidizing agents, more preferentially hydrogen peroxide.

According to one embodiment, the treatment process consists in applying the composition as defined previously to keratin materials.

Preferably, the treatment process consists in applying the composition as defined previously on dry or wet keratin fibres. The composition is left in place on the fibres for a period, generally from 1 minute to 1 hour, preferably from 5 minutes to 30 minutes.

The temperature during the process is conventionally between room temperature (between 15% and 25° C.) and 80° C. and preferably between room temperature and 60° C.

Preferentially, the composition is applied at room temperature.

After the treatment, the keratin materials are optionally rinsed with water, optionally washed with a shampoo and then rinsed with water, before being dried or left to dry.

The composition according to the invention may be prepared by mixing at least two compositions.

The composition according to the invention may especially be obtained by mixing two compositions:
- a composition (A) comprising one or more compounds of formula (I) according to the invention, and
- a composition (B) comprising one or more chemical oxidizing agents.

Compounds of Formula (II) and Corresponding Composition

As indicated previously, the present invention also relates to compounds of formula (II) as defined previously, and also the addition salts thereof and/or the solvates thereof.

The compound(s) of formula (II), and also the tautomeric forms thereof, the addition salts thereof and/or the solvates thereof, may be present in the composition according to the invention in a content that may range from 0.01% to 10% by weight, preferably in a content ranging from 0.5% to 3% by weight, more preferably in a content ranging from 1% to 3% by weight, relative to the total weight of the composition.

The composition preferentially comprises a physiologically acceptable medium.

Compounds of Formula (III) and Corresponding Composition

As indicated previously, the present invention also relates to compounds of formula (III) as defined previously, and also the tautomeric forms thereof, the addition salts thereof and/or the solvates thereof.

Preferably, $L_1$ represents:
- a linear or branched, saturated $C_1$-$C_{15}$ alkylene radical, optionally substituted with one or more hydroxyl groups,
- a $C_1$-$C_{15}$ alkylene radical, one or more carbon atoms of which are interrupted with one or more non-adjacent heteroatoms chosen from oxygen, nitrogen and sulfur.

The preferred compounds of formula (III) are such that:
$R_{21}$, $R_{22}$, $R_{25}$ and $R_{26}$ represent, independently of each other, a radical chosen from:
- a hydrogen atom,
- a halogen atom,
- a $C_1$-$C_6$ alkyl radical optionally substituted with one or more groups, which may be identical or different, chosen from hydroxyl, $C_1$-$C_6$ alkoxy, cyano and amino —$NR_aR_b$ groups,
- a $C_1$-$C_6$ alkoxy radical;
- a hydroxyl radical,
- an amino radical —$NR_aR_b$, and
preferably, chosen from a hydrogen atom and a $C_1$-$C_4$ alkyl radical, $R_{27}$, $R_{28}$, $R_{29}$ and $R_{30}$ represent, independently of each other, a radical chosen from:
- a hydrogen atom,
- a $C_1$-$C_6$ alkyl radical optionally substituted with one or more groups, which may be identical or different, chosen from hydroxyl, $C_1$-$C_6$ alkoxy, cyano and amino —$NR_aR_b$ groups,
- a $C_3$-$C_6$ alkoxy radical,
- a halogen atom,
- a hydroxyl radical,
- an amino radical —$NR_aR_b$, and
preferably, chosen from a hydrogen atom and a $C_1$-$C_4$ alkyl radical, $R_{24}$ represents a $C_1$-$C_6$ alkyl radical optionally substituted with one or more groups, which may be identical or different, chosen from hydroxyl, $C_1$-$C_6$ alkoxy, cyano, amino —$NR_aR_b$, aminocarbonyl —$CONH_2$ and carboxyl —$CO_2H$ groups, and preferably a $C_1$-$C_4$ alkyl radical optionally substituted with a $C_1$-$C_4$ alkyl radical optionally substituted with a $C_1$-$C_6$ alkoxy group such as methoxy, $L_1$ preferentially represents:
- a linear or branched, saturated $C_1$-$C_{10}$ alkylene radical, optionally substituted with one or more hydroxyl groups,
- a $C_1$-$C_{10}$ alkylene radical, one or more carbon atoms of which are interrupted with one or more non-adjacent heteroatoms chosen from oxygen, nitrogen and sulfur, $R_a$ and $R_b$ represent, independently of each other, a hydrogen atom or a linear or branched, saturated or unsaturated $C_1$-$C_6$ alkyl radical.

More preferentially, the compounds of formula (III) are such that:
$R_{21}$, $R_{22}$, $R_{24}$, $R_{25}$, $R_{26}$, $R_{30}$, $R_{27}$, $R_{28}$ and $R_{29}$ denote a hydrogen atom, $R_{24}$ represents a $C_1$-$C_6$ alkyl radical optionally substituted with one or more groups, which may be identical or different, chosen from hydroxyl, $C_1$-$C_6$ alkoxy, cyano, amino —$NR_aR_b$, aminocarbonyl —$CONH_2$ and carboxyl —$CO_2H$ groups, and preferably a $C_1$-$C_4$ alkyl radical optionally substituted with a $C_1$-$C_6$ alkoxy group such as methoxy, $L_1$ represents:
- a linear or branched, saturated $C_1$-$C_{10}$ alkylene radical, optionally substituted with one or more hydroxyl groups,
- a $C_1$-$C_{10}$ alkylene radical, one or more carbon atoms of which are interrupted with one or more non-adjacent heteroatoms chosen from oxygen, nitrogen and sulfur.

$R_a$ and $R_b$ represent, independently of each other, a hydrogen atom or a linear or branched, saturated or unsaturated $C_1$-$C_6$ alkyl radical.

The compounds of formula (III), the tautomeric forms thereof, the addition salts thereof and/or the solvates thereof are chosen from compounds (10) to (19) as described previously.

The compound(s) of formula (III), and also the tautomeric forms thereof, the addition salts thereof and/or the solvates thereof, may be present in the composition according to the invention in a content that may range from 0.01% to 10% by weight, preferably in a content ranging from 0.5% to 3% by weight, more preferably in a content ranging from 1% to 3% by weight, relative to the total weight of the composition.

The composition preferentially comprises a physiologically acceptable medium.

Compounds of Formula (IV) and Corresponding Composition

As indicated previously, the present invention also relates to compounds of formula (IV) as defined previously, and also the tautomeric forms thereof, the addition salts thereof and/or the solvates thereof.

Preferably, $L_2$ represents:
- a linear or branched, saturated or unsaturated, unsubstituted $C_4$-$C_9$ alkylene radical,
- a $C_1$-$C_{15}$ alkylene radical substituted with one or more hydroxyl groups,
- a $C_1$-$C_{15}$ alkylene radical, one or more carbon atoms of which are interrupted with one or more non-adjacent heteroatoms chosen from oxygen, nitrogen and sulfur.

Preferably, $L_2$ represents:
- a linear or branched, saturated, unsubstituted $C_4$-$C_9$ alkylene radical, a $C_2$-$C_{10}$ alkylene radical substituted with one or more hydroxyl groups, a $C_2$-$C_{10}$ and preferably $C_4$-$C_9$ alkylene radical, one or more carbon atoms of which are interrupted with one or more non-adjacent heteroatoms chosen from oxygen, nitrogen and sulfur.

The preferred compounds of formula (IV) are such that:

$R_{31}$, $R_{32}$, $R_{33}$, $R_{35}$ and $R_{36}$ represent, independently of each other, a radical chosen from:

a hydrogen atom;

a halogen atom, a $C_1$-$C_6$ alkyl radical optionally substituted with one or more groups, which may be identical or different, chosen from hydroxyl, $C_1$-$C_6$ alkoxy, cyano and amino —$NR_aR_b$ groups, a $C_1$-$C_6$ alkoxy radical, a hydroxyl radical;

an amino radical —$NR_aR_b$, and preferably chosen from a hydrogen atom and a $C_1$-$C_4$ alkyl radical, $R_{37}$, $R_{38}$, $R_{39}$ and $R_{40}$ represent, independently of each other, a radical chosen from:

a hydrogen atom;

a halogen atom, a $C_1$-$C_6$ alkyl radical optionally substituted with one or more groups, which may be identical or different, chosen from hydroxyl, $C_1$-$C_6$ alkoxy, cyano and amino —$NR_aR_b$ groups, a hydroxyl radical, an amino radical —$NR_aR_b$, and preferably chosen from a hydrogen atom and a $C_1$-$C_4$ alkyl radical, it being understood that $R_{38}$ and $R_{39}$ cannot simultaneously denote a $C_1$ alkoxy radical, $R_a$ and $R_b$ represent, independently of each other, a hydrogen atom or a linear or branched, saturated or unsaturated $C_1$-$C_6$ alkyl radical, $L_2$ represents:

a linear or branched, saturated, unsubstituted $C_4$-$C_9$ alkylene radical, a $C_1$-$C_{15}$ alkylene radical substituted with one or more hydroxyl groups, a $C_1$-$C_{15}$ alkylene radical, one or more carbon atoms of which are interrupted with one or more non-adjacent heteroatoms chosen from oxygen, nitrogen and sulfur.

More particularly, the preferred compounds of formula (IV) are such that:

$R_{31}$, $R_{32}$, $R_{33}$, $R_{35}$, $R_{36}$, $R_{37}$, $R_{38}$, $R_{39}$ and $R_{40}$ denote a hydrogen atom, $L_2$ represents:

a linear or branched, saturated $C_4$-$C_9$ alkylene radical, a $C_2$-$C_{10}$ alkylene radical substituted with one or more hydroxyl groups, a $C_2$-$C_{10}$ and preferably $C_4$-$C_9$ alkylene radical, one or more carbon atoms of which are interrupted with one or more non-adjacent heteroatoms chosen from oxygen, nitrogen and sulfur.

The compounds of formula (IV), the tautomeric forms thereof, the addition salts thereof and/or the solvates thereof are chosen from compounds 1 and 4 to 9 as described previously, in particular compound 1 (2,2'-butane-1,4-diyldi-3,4 dihydroisoquinolinium dibromide).

The compound(s) of formula (IV), and also the tautomeric forms thereof, the addition salts thereof and/or the solvates thereof, may be present in the composition according to the invention in a content that may range from 0.01% to 10% by weight, preferably in a content ranging from 0.5% to 3% by weight, more preferably a content ranging from 1% to 3% by weight, relative to the total weight of the composition.

The composition preferentially comprises a physiologically acceptable medium.

Process for Preparing the Compounds of Formula (IV)

The compounds of formula (IV) may be obtained by quaternization of dihydroisoquinoline derivatives (1) with alkylating reagents (2). This reaction generally takes place in the presence of a solvent, for instance ethanol, and is accelerated by heating.

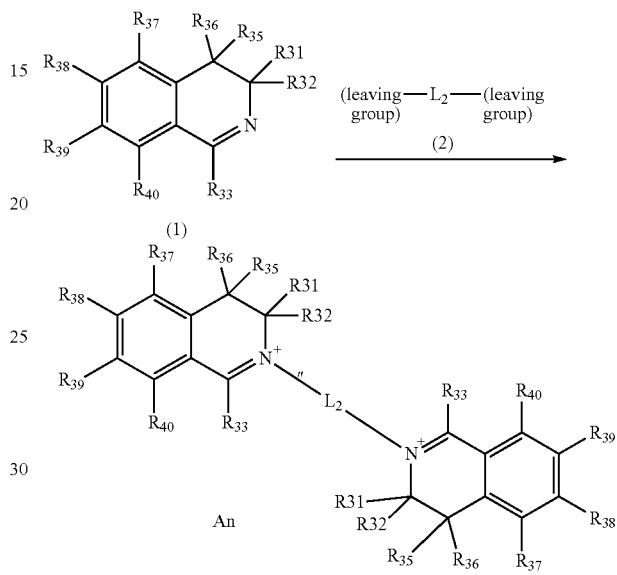

The compounds of formula (IV) may also be obtained by simple counter-anion exchange with a salt of the anion ensuring the electrical neutrality:

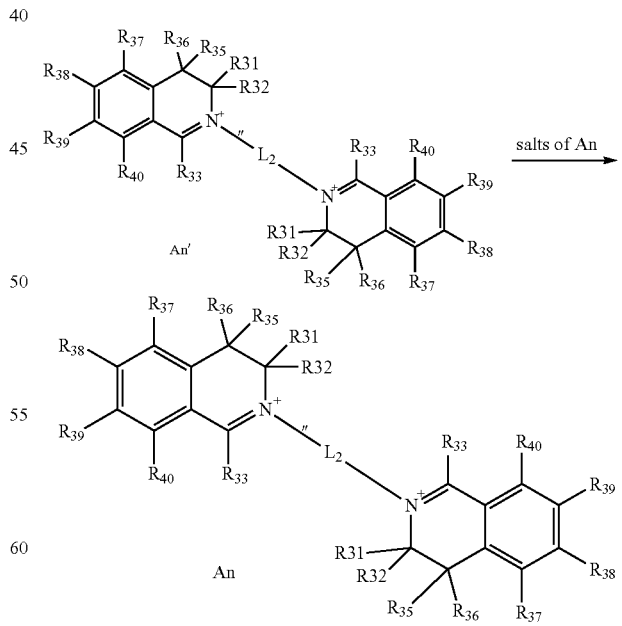

More generally, the compounds of formulae (II), (III) and (IV) may be obtained by drawing on the bibliographic references below: Archiv der Pharmazie (Weinheim, Germany), 1988, vol. 321, pages 759-764, Journal of Organic Chemistry, 2014, vol. 10, pages 2981-2988, Tetrahedron, 2012, vol. 68, 26 pages 5137-5144, Heterocycles, 2004, vol. 63, 2 pages 401-409, Green Chemistry, 2014, vol. 16, 10 pages 4524-4529, Journal of Organic Chemistry, 1982, vol. 47, 12 pages 2308-2312, Tetrahedron, 1993, vol. 49, 2 pages 423-438, Synthesis, 1992, 9 pages 887-890, Journal of the American Chemical Society, 1949, vol. 71, pages 3405, 3407, Tetrahedron Letters, 1987, vol. 28, 48 pages 6061-6064, Journal of Medicinal Chemistry (1971), 14(7), 580-3, GB 1 125 619 (1968), Journal of the American Chemical Society (1958), 80, 1451-6, Journal of the Chemical Society (1929), 2010-21.

In particular, to synthesize the compounds of formula (II), the synthesis of compound 1 may be adapted according to the nature of the desired substituents.

To synthesize the compounds of formula (IV), it will be possible, for example, to adapt the synthesis described in Chem. Ber., 1963, 96 (7), 1779-87 according to the nature of the desired substituents.

The compounds of structure (III) may be synthesized by adapting the synthesis described in GB 1 125 619 or J. Chem. Soc., 1929, 2010-21, according to the nature of the desired substituents.

Particularly, the compound(s) of formula (I) according to the invention are used in the presence of one or more chemical oxidizing agents for improving the lightening of keratin materials, especially keratin fibres, preferably human keratin fibres such as the hair.

In other words, the compound(s) of formula (I) according to the invention are used for improving the oxidizing activity of one or more chemical oxidizing agents.

Preferably, the chemical oxidizing agent is hydrogen peroxide.

The examples that follow serve to illustrate the invention without, however, being limiting in nature.

In these examples, the colour of the locks was evaluated in the CIE L* a* b* system, using a Minolta Spectrophotometer CM2600D colorimeter.

In this L* a* b* system, the three parameters denote, respectively, the colour intensity (L*), the green/red colour axis (a*) and the blue/yellow colour axis (b*). The higher the value of L*, the lighter the colour. The higher the value of a*, the redder the colour and the higher the value of b*, the yellower the colour.

EXAMPLE

Example 1

Synthesis of 2,2'-butane-1,4-diyldi-3,4-dihydroisoguinolinium dibromide (compound 1)

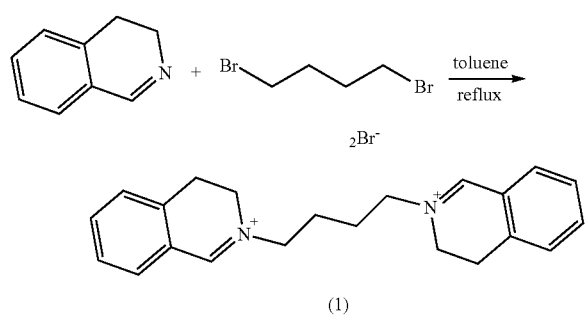

(1)

10 g of 3,4-dihydroisoquinoline (4 eq.) are placed in a 250 mL three-necked flask in 75 mL of toluene, followed by addition of 2.28 mL of 1,4-dibromobutane (1 eq.). The mixture is refluxed with vigorous stirring for 15 hours. The beige-brown precipitate is filtered off under vacuum and under argon and washed with diisopropyl ether and then dried under vacuum over $P_2O_5$.

The product is recrystallized from 80 mL of n-propanol and is isolated in the form of a beige-coloured powder (5.15 g, yield=56.5%).

The analyses are in accordance with the expected product.

Example 2

I. Preparation of the Compositions
The following formulations are prepared:
Preparation of Formulation A:

| Chemical name | g % |
|---|---|
| 2-Octyldodecanol | 11.5 |
| Liquid petroleum jelly | 74.5 |
| Oxyethylenated lauryl alcohol (2 OE) | 3 |
| Oxyethylenated sorbitan mono laurate (4 OE) | 11 |

Preparation of the Oxidizing Formulation B (HQ2):

| Chemical name | g % |
|---|---|
| Glycerol | 0.5 |
| (50% linear 70/30 $C_{13}/C_{15}$)alkyl ether carboxylic acid monoethanolamide (2 OE) | 0.85 |
| Tetrasodium pyrophosphate decahydrate | 0.02 |
| 50% hydrogen peroxide solution (200 vol. aqueous hydrogen peroxide solution) | 12 |
| Disodium tin hexahydroxide | 0.04 |
| Diethylenetriaminepentaacetic acid, pentasodium salt as an aqueous 40% solution | 0.15 |
| Cetylstearyl alcohol/oxyethylenated (30 OE) cetylstearyl alcohol mixture | 2.85 |
| Deionized water | 83.59 |

Preparation of Compositions 1 and 2 for Evaluation on Locks:

Compositions 1 to 2 were obtained from the following ingredients:

| | Composition 1 | Composition 2 |
|---|---|---|
| 2,2'-Butane-1,4-diyldi-3,4 dihydroisoquinolinium dibromide (1) | — | 30 mg |
| Formulation A | 1 g | 1 g |
| Oxidizing formulation B ($H_2O_2$) | 1.5 g | 1.5 g |
| 20% Aqueous ammonia $NH_4OH$ | Drops → pH = 9.5 | Drops → pH = 9.5 |

After preparation, compositions 1 and 2 are applied to natural 250 mg locks with a tone depth of 4. After a leave-on time of 30 minutes at a temperature of 27° C., the locks are washed with shampoo, rinsed and dried.

The colorimetric data are then measured with a Minolta CM-3610d spectrophotometer:

| | Composition 1 | Composition 2 |
|---|---|---|
| Lightening (L*) | 23.8 | 29.5 |

It is noted that greater lightening is obtained with composition 2 according to the invention than with composition 1.

In particular, it is noted that the presence of the dihydroisoquinolinium double salts makes it possible to improve the oxidizing power of hydrogen peroxide and thus to boost its activity (comparison between composition 1 and composition 2).

The invention claimed is:

1. A method for lightening human hair, the method comprising:
applying to said human hair at least one compound of formula (I), the tautomeric forms thereof, the addition salts thereof, or the solvates thereof optionally in the presence of at least one chemical oxidizing agent:

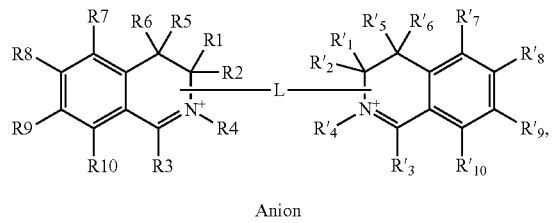

Anion wherein in formula (I):
$R_1$, $R_2$, $R_3$, $R_5$, $R_6$, $R_7$, $R_8$, $R_9$, $R_{10}$, $R'_1$, $R'_2$, $R'_3$, $R'_5$, $R'_6$, $R'_7$, $R'_8$, $R'_9$ and $R'_{10}$, independently of each other, are chosen from:
a hydrogen atom;
a halogen atom,
a $C_1$-$C_6$ alkyl radical optionally substituted with at least one group, which may be identical or different, chosen from hydroxyl, $C_1$-$C_6$ alkoxy, cyano, or amino —$NR_aR_b$ groups,
a $C_1$-$C_6$ alkoxy radical;
a hydroxyl radical;
an amino radical —$NR_aR_b$,
an aminocarbonyl radical —$CONH_2$, or
a carboxyl radical —$CO_2H$,
$R_4$ and $R'_4$ together form a divalent radical L such that L is chosen from a linear or branched, saturated or unsaturated $C_1$-$C_{15}$ alkylene radical, optionally substituted with at least one hydroxyl group and/or interrupted with at least one non-adjacent heteroatom chosen from oxygen, nitrogen, or sulfur,
$R_a$ and $R_b$ are chosen from, independently of each other, a hydrogen atom or a linear or branched, saturated or unsaturated $C_1$-$C_6$ alkyl radical,
Anion denotes an organic or mineral anion or mixture of anions which ensures the electrical neutrality of the compounds of formula (I).

2. The method according to claim 1, wherein a radical chosen from the radicals $R_i$ and a radical chosen from the radicals $R'_j$ when i=j, together form:
a divalent radical L representing a linear or branched, saturated or unsaturated $C_1$-$C_{15}$ alkylene radical, optionally substituted with at least one hydroxyl group and/or interrupted with at least one non-adjacent heteroatom chosen from oxygen, nitrogen, or sulfur, or
a single bond.

3. The method according to claim 1, wherein a radical chosen from the radicals $R_i$ and a radical chosen from the radicals $R'_j$ when i and j are identical and are equal to 3 or 4, together form a divalent radical L, or a covalent single bond.

4. The method according to claim 1, wherein:
$R_1$ and $R'_1$ are identical to each other, $R_2$ and $R'_2$ are identical to each other, $R_3$ and $R'_3$ are identical to each other, $R_5$ and $R'_5$ are identical to each other, $R_6$ and $R'_6$ are identical to each other, $R_7$ and $R'_7$ are identical to each other, $R_8$ and $R'_8$ are identical to each other, $R_9$ and $R'_9$ are identical to each other, $R_{10}$ and $R'_{10}$ are identical to each other and, independently from one pair to another, are chosen from
a hydrogen atom;
a halogen atom,
a $C_1$-$C_6$ alkyl radical optionally substituted with at least one group, which may be identical or different, chosen from hydroxyl, cyano, $C_1$-$C_6$ alkoxy, or amino $NR_aR_b$ groups,
a $C_1$-$C_6$ alkoxy radical;
a hydroxyl radical;
an amino radical $NR_aR_b$,
an aminocarbonyl radical —$CONH_2$, or
a carboxyl radical —$CO_2H$,
$R_4$ and $R'_4$ together form a divalent radical L such that L is chosen from a linear or branched, saturated or unsaturated $C_1$-$C_{15}$ alkylene radical, optionally substituted with at least one hydroxyl group and/or interrupted with at least one non-adjacent heteroatom chosen from oxygen, nitrogen, or sulfur,
$R_a$ and $R_b$, independently of each other, are chosen from a hydrogen atom or a linear or branched, saturated or unsaturated $C_1$-$C_6$ alkyl radical.

5. The method according to claim 1, wherein:
$R_1$, $R'_1$, $R_2$, $R'_2$, $R_3$, $R'_3$, $R_5$, $R'_5$, $R_6$, $R'_6$, $R_7$, $R'_7$, $R_8$, $R'_8$, $R_9$ and $R'_9$ denote a hydrogen atom,
$R_4$ and $R'_4$ together form a divalent radical L such that L represents a saturated linear $C_1$-$C_{15}$ alkylene radical, optionally substituted with at least one hydroxyl group or interrupted with at least one non-adjacent heteroatom chosen from oxygen, nitrogen, or sulfur, L optionally denoting a saturated, linear or branched $C_2$-$C_{10}$ alkylene radical, optionally substituted with at least one hydroxyl group or interrupted with at least one non-adjacent heteroatom chosen from oxygen.

6. The method according to claim 1, wherein the at least one compound of formula (I), the tautomeric forms thereof, the addition salts thereof, and/or the solvates thereof are chosen from the following compounds, the tautomeric forms thereof, the addition salts thereof, and/or the solvates thereof:

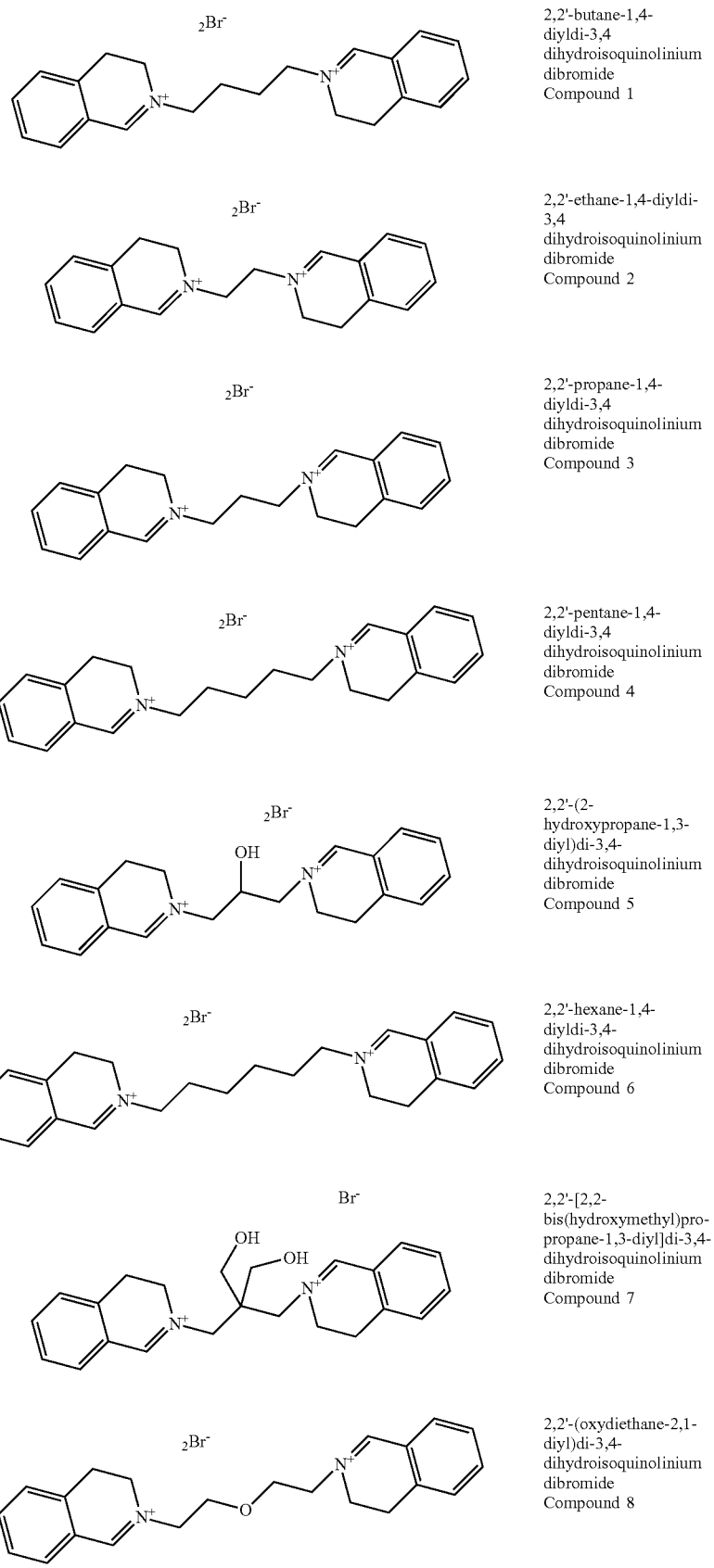

| | |
|---|---|
| | 2,2'-butane-1,4-diyldi-3,4 dihydroisoquinolinium dibromide Compound 1 |
| | 2,2'-ethane-1,4-diyldi-3,4 dihydroisoquinolinium dibromide Compound 2 |
| | 2,2'-propane-1,4-diyldi-3,4 dihydroisoquinolinium dibromide Compound 3 |
| | 2,2'-pentane-1,4-diyldi-3,4 dihydroisoquinolinium dibromide Compound 4 |
| | 2,2'-(2-hydroxypropane-1,3-diyl)di-3,4-dihydroisoquinolinium dibromide Compound 5 |
| | 2,2'-hexane-1,4-diyldi-3,4-dihydroisoquinolinium dibromide Compound 6 |
| | 2,2'-[2,2-bis(hydroxymethyl)propropane-1,3-diyl]di-3,4-dihydroisoquinolinium dibromide Compound 7 |
| | 2,2'-(oxydiethane-2,1-diyl)di-3,4-dihydroisoquinolinium dibromide Compound 8 |

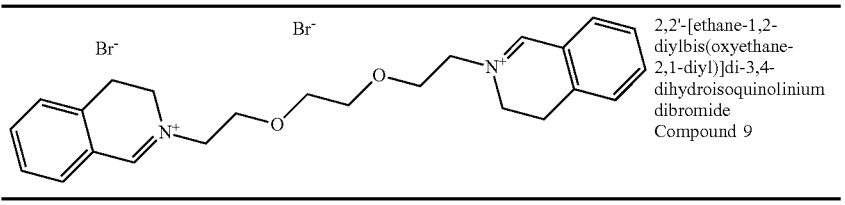

2,2'-[ethane-1,2-diylbis(oxyethane-2,1-diyl)]di-3,4-dihydroisoquinolinium dibromide
Compound 9 or mixtures thereof.

7. A method for improving the oxidizing activity of at least one chemical oxidizing agent, the method comprising:
applying to human hair at least one compound of formula (I), the tautomeric forms thereof, the addition salts thereof, or the solvates thereof in the presence of at least one chemical oxidizing agent:

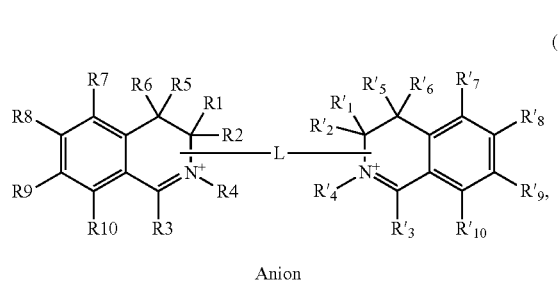

wherein in formula (I):
$R_1$, $R_2$, $R_3$, $R_5$, $R_6$, $R_7$, $R_8$, $R_9$, $R_{10}$, $R'_1$, $R'_2$, $R'_3$, $R'_5$, $R'_6$, $R'_7$, $R'_8$, $R'_9$ and $R'_{10}$, independently of each other, are chosen from:

a hydrogen atom;
a halogen atom,
a $C_1$-$C_6$ alkyl radical optionally substituted with at least one group, which may be identical or different, chosen from hydroxyl, $C_1$-$C_6$ alkoxy, cyano, or amino —$NR_aR_b$ groups,
a $C_1$-$C_6$ alkoxy radical;
a hydroxyl radical;
an amino radical —$NR_aR_b$,
an aminocarbonyl radical —$CONH_2$, or
a carboxyl radical —$CO_2H$,
$R_4$ and $R'_4$ together form a divalent radical L such that L is chosen from a linear or branched, saturated or unsaturated $C_1$-$C_{15}$ alkylene radical, optionally substituted with at least one hydroxyl group and/or interrupted with at least one non-adjacent heteroatom chosen from oxygen, nitrogen, or sulfur
$R_a$ and $R_b$ are chosen from, independently of each other, a hydrogen atom or a linear or branched, saturated or unsaturated $C_1$-$C_6$ alkyl radical,
Anion denotes an organic or mineral anion or mixture of anions which ensures the electrical neutrality of the compounds of formula (I).

* * * * *